United States Patent
Bucalo

[11] 3,958,561
[45] May 25, 1976

[54] METHODS AND DEVICES FOR COLLECTING BODY FLUIDS

[75] Inventor: Louis Bucalo, Holbrook, N.Y.

[73] Assignee: Microbyx Corporation, Holbrook, N.Y.

[22] Filed: July 24, 1974

[21] Appl. No.: 491,506

Related U.S. Application Data

[63] Continuation-in-part of Ser. No. 329,671, Feb. 5, 1973, Pat. No. 3,867,924.

[52] U.S. Cl. .............................. 128/2 F; 128/272; 128/285
[51] Int. Cl.² .......................................... A61B 10/00
[58] Field of Search ...... 128/2 F, 2 W, 270, DIG. 5, 128/269, 268, 285, 296, 276, 277, 278, 127, 272, 2 B, 2 G; 73/425.4 P, 425.6

[56] References Cited
UNITED STATES PATENTS

| | | | |
|---|---|---|---|
| 2,110,962 | 3/1938 | Munro | 128/285 X |
| 3,221,741 | 12/1965 | Le Veen | 128/214 R |
| 3,420,107 | 1/1969 | Rowett | 73/425.6 |
| 3,430,628 | 3/1969 | Wiggins | 128/276 |
| 3,520,300 | 7/1970 | Flower, Jr. | 128/276 |
| 3,559,646 | 2/1971 | Mullan | 128/270 |
| 3,838,681 | 10/1974 | Dalton | 128/2 W X |

Primary Examiner—Dalton L. Truluck
Attorney, Agent, or Firm—Steinberg and Blake

[57] ABSTRACT

Methods and devices according to which body fluids, such as blood, are collected in the interior of the body in a cavity thereof with the fluid which is collected being directed to a fluid receiving location through a path of a given degree of restriction for controlling the characteristics of the collected fluid. Thus, it is possible to direct a fluid such as blood to the interior of a container through a suitable filter or sponges of different degree of coarseness can be arranged with one surrounding the next with each inner sponge having cells smaller than the next outer sponge. Also it is possible to utilize receptacles communicating through capillary tubes of predetermined diameters with the fluid. A suitable preservative for the body fluid is situated in the container.

11 Claims, 4 Drawing Figures

METHODS AND DEVICES FOR COLLECTING BODY FLUIDS

CROSS REFERENCE TO RELATED APPLICATION

This application is a continuation-in-part of copending application Ser. No. 329,671, filed Feb. 5, 1973 and entitled "Internal Blood Collection", now U.S. Pat. No. 3,867,924 which issued on Feb. 25, 1975.

BACKGROUND OF THE INVENTION

The present invention relates to methods and devices for collecting body fluids such as blood so that the fluid can thereafter be analyzed.

While it has already been proposed to collect a fluid such as blood which is present in the interior of a body cavity, it is often desirable to be able to control the characteristics of the collected fluid. Up to the present time it has not been possible to achieve this result since the fluid such as blood is simply collected in the manner in which it is found in a body cavity, and therefore when subsequently tested the fluid may not have characteristics which are suitable for giving the required information in the fastest and most convenient manner.

SUMMARY OF THE INVENTION

It is accordingly a primary object of the present invention to provide methods and devices which will solve the above problem.

It is in particular an object of the present invention to provide methods and devices which may be used for collection and testing of blood which is to be found in the interior of the body. For example the methods and devices of the present invention may be used in the vagina during menstrual flow for collecting menstrual blood.

It is in particular an object of the present invention to provide methods and devices which will restrict the flow of the body fluid in such a way that the collected blood will have predetermined characteristics.

Also it is an object of the present invention to provide methods and devices which can conveniently have the fluid, such as blood, treated by suitable additives for giving the fluid which is subsequently tested desired characteristics.

In addition, it is an object of the present invention to provide methods and devices which enable the collected blood or the like to be transported, by mail, for example, to a testing location such as a suitable laboratory.

According to the method of the invention there is introduced into a body cavity, where a fluid, such as blood, is present, a device which has an interior for receiving and holding the fluid as well as a passage means which restricts the flow of fluid to the interior of the device to a predetermined extent for controlling the characteristics of the fluid received in the interior of the device. Thereafter the device is removed and the collected fluid is tested.

The device of the invention has a receiving means capable of receiving and holding a fluid, such as blood, with a passage means communicating with the receiving means for directing the blood or the like thereto. The passage means provides a predetermined restriction to the flow of fluid to the receiving means so as to control the characteristics of the fluid collected thereby.

BRIEF DESCRIPTION OF DRAWINGS

The invention is illustrated by way of example in the accompanying drawings which form part of this application and in which.

DESCRIPTION OF PREFERRED EMBODIMENTS

Figure 1:
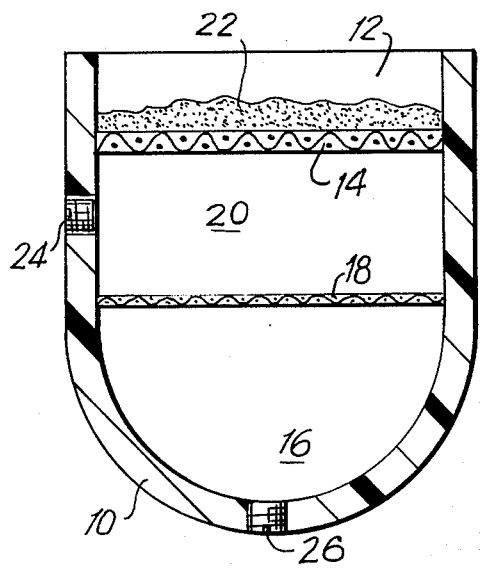
FIG. 1 is a sectional elevation of one embodiment of a device of the invention for carrying out the method of the invention.

Referring first to FIG. 1, there is shown therein a container 10 made of any suitable plastic, for example, and capable of being situated in a body cavity such as the vagina. When thus introduced into a cavity such as the vagina, the container 10 is oriented so that its open end 12, shown at the upper part of FIG. 1, is directed toward the blood or other body fluid which thus will flow downwardly, as viewed in FIG. 1, into the interior of the container 10. The hollow interior portion of the container 10 forms a receiving means capable of receiving the fluid such as the blood.

The container 10 fixedly carries adjacent its open end 12 a relatively coarse filter 14 which extends across the interior of the container 10 in the manner illustrated, the outer periphery of the filter 14 being fixed to the inner surface of the container 10 in any suitable way. For example, where the container 10 is made of plastic the wall of the container 10 may be molded directly onto the periphery of the filter 14 or the filter 14 may be suitably glued to the interior of the container 10 or fastened thereto in any suitable way.

Between the filter 14 and the innermost interior portion 16 of the container 10 is a second filter 18 which is finer than the filter 14 and which is fixed to the interior of the container 10 in the position illustrated. Of course the filter 18 will be fixed to the container 10 before the filter 14 and this filter 18 which is finer than the filter 14 can be fixed to the inner surface of the container 10 in the same way as the filter 14. In this way the innermost interior portion 16 is separated from an interior portion 20 by the filter 18 with this interior portion 20 being defined between the relatively coarse filter 14 and the relatively fine filter 18. Thus, the container 10 has a pair of interior portions 16 and 20 capable of receiving blood when introduced into a body cavity where blood is situated. Thus where the container 10 is introduced into the vagina, the menstrual blood will flow first through the coarse filter 14 and then through the fine filter 18 so that the fluid portion in the region 20 will have characteristics different from the filtrate of menstrual flow which will become situated in the interior portion 16. Thus, fluid in region 20 will have, for example, mucous not present in the clear fluid in region 16. It will be noted that the filters 14 and 18 form a passage means providing a predetermined degree of restriction of fluid flow to the receiving means formed respectively by the interior portions 20 and 16. In the case of menstrual flow, various mucoid and solid components 22 will be retained by the filter 14 between the latter and the open end 12, this material 22 forming the endometrium which can be tested when the device 10 is removed from the vagina. For example, the endometrium can be tested for cancer of the cervix. The fluid portion retained in the chamber 20 between the filters 14 and 18 can be discharged upon removal of a plug 24 which is threaded into an opening in a side wall portion of the container 10 as illustrated in FIG. 1. The filtrate in the innermost chamber 16 can be discharged upon removal of a plug 26 which is threaded into a suitable opening formed at the lower end of a container 10 as illustrated in FIG. 1. Thus the plugs 24 and 26 are capable of closing the chambers 20 and 16, respectively, so that fluids will be retained therein while after the container 10 is removed from the body cavity these fluids can be discharged upon removal of the plugs so as to be tested.

It is possible to situate in the chamber 16, for example, one or more additives which will provide the collected fluid with desired characteristics. For example, these additives may take the form of red cell stabilizers and/or agglutinins. Also the additive can include an antibacterial or a general germicide, as well as any desired surfactants or detergents. In addition it is possible to provide an additive to prevent hemolysis, such as Dextran. Also, an additive may be provided to stabilize the red cell membrane, tannic acid being a suitable additive for this purpose. In addition it is possible to provide an additive such as soybean agglutinins for clotting the red cells.

Thus, after the device of FIG. 1 has remained in the body cavity for a time sufficient for collection of body fluid it is removed from the body cavity and then the body fluids and/or the material such as the endometrium 22 are tested. Thus in the case of the vagina the material 22 will include cervical mucosa or endometrium which may indicate cancer. Of course, the various fluids may be cultured to test for the presence of suspected microorganisms.

Figure 2:
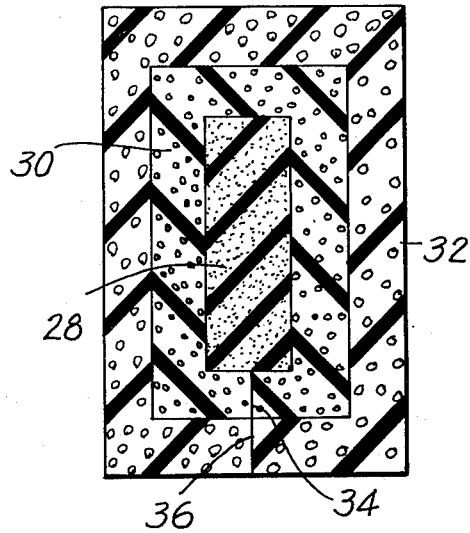
FIG. 2 is a sectional elevation of another embodiment of a device of the invention for carrying out the method of the invention.

Instead of a device and method as described above in connection with FIG. 1, it is also possible to use a device and method as illustrated in FIG. 2. According to FIG. 2 the device includes a plurality of sponge-type bodies. In the example shown in FIG. 2 there is an innermost sponge body 28 which has cells smaller than those of the next outermost spong body 30 which completely surrounds and encloses the sponge body 28, entirely enveloping the latter as illustrated in FIG. 2. In turn the sponge body is completely surrounded and enveloped by the outermost sponge body 32 which has cells larger than those of the sponge body 30 with the cells of the sponge body 30 of course being larger than those of the innermost sponge body 28. The sponge body 30 may be placed around the body 28 with surfaces of the body 30 being joined at the plane 34, while the outermost body 32 can then be placed around the body 30 with surfaces joined at plane 36 which coincides with the plane 34.

The device of FIG. 2 can also be inserted into any body cavity such as the vagina for collecting a fluid such as blood. Because of the different degrees of fineness of the cells of the successive sponge bodies, the fluid collected by the innermost sponge body 28 will have characteristics different from those collected by the sponge body 30 while the sponge body 30 will in turn have fluid whose characteristics differ from those collected by the outermost sponge body 32. In this case also the outer surface of the sponge body 32 will be engaged by a certain amount of a material such as the endometrium 22 which can also be checked in the event that the device of FIG. 2 is inserted into the vagina.

When the device of FIG. 2 is removed from the body cavity after having remained therein for a time sufficient to collect a fluid such as blood, the outermost body 32 can be separated at the plane 36 from the next inner body 30, and the fluid in the cells of the outermost sponge body 32 can be squeezed out of the latter and tested. In the same way the next inner body 30 can be separated at plane 34 to be removed from the innermost sponge body 28 and then the fluid retained by the cells of the body 30 can be squeezed out of the latter and tested. Finally the clearest fluid retained by the body 28 can be squeezed out of the latter and tested. In this case also it is possible to impregnate a body such as the bodies 28 or 30 with any one of the additives referred to above in connection with FIG. 1. Thus in the case of FIG. 2 it is the sponge bodies which form the passage means and receiving means with each outer sponge body forming a passage means providing a given degree of restriction of flow of fluid to the next inner sponge body which forms a receiving means. Thus the body 30 will form a receiving means with respect to the body 32 and a passage means with respect to the body 28. Of course the innermost body 28 functions only as a receiving means.

Figure 3:
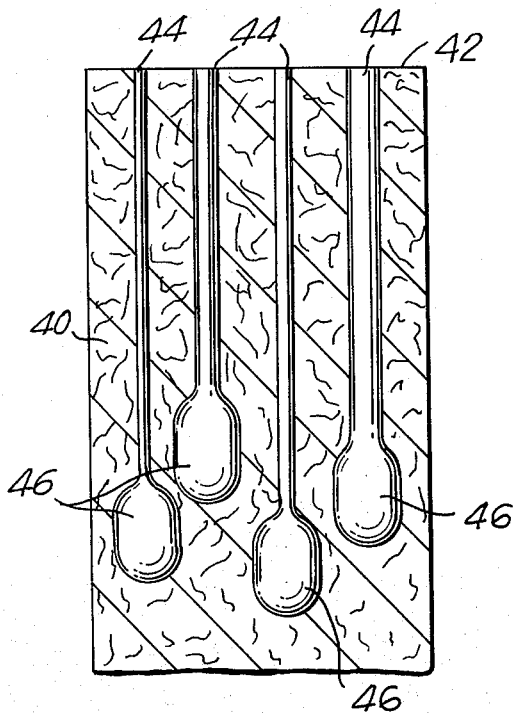
FIG. 3 is a fragmentary partly sectional elevation of a further embodiment of a device of the invention for carrying out the method of the invention.

It is also possible to provide a method and device as illustrated in FIG. 3. Thus, FIG. 3 illustrates a portion 40 of a tampon made of cotton wadding or the like. This tampon is of the type which is introduced into the vagina during the menstrual period. The elongated tampon 40 has an end surface 42 where a plurality of capillary tubes 44 have open ends. When the tampon 40 is introduced into the vagina the end surface 42 is introduced first so that the blood will be received at the exposed open ends of the several capillary tubes 44 which are illustrated in FIG. 3. These capillary tubes 44 respectively communicate with hollow receptacles 46, and it will be seen that the capillary tubes 44 and the receptacles 46 communicating therewith are embedded in the tampon 40 in such a way that only the open ends of the tubes 44 distant from the receptacles 46 are exposed to receive blood. It will be seen from FIG. 3 various capillary tubes 44 have different diameters so that in this way they provide passages having different degrees of restriction of flow to the several receptacles 46. Thus, the tube 44 shown at the left in FIG. 3 has the smallest diameter and provides the smallest restriction so that the clearest fluid will be received in the left receptacle 46. The graduated tubes 44 of different diameters will provide different degrees of restriction to the flow of fluid so that in this way the different receptacles 46 will have different characteristics with different materials being included. For example, the largest tube 44 may permit certain small solid particles to be incorporated into the fluid received in the receptacle 46 which communicates therewith.

Figure 4:
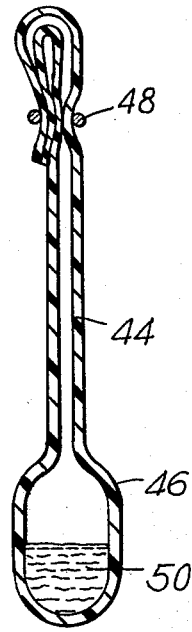
FIG. 4 is a sectional elevation, enlarged as compared to FIG. 3, of one of the receptacles and capillary tubes of FIG. 3 shown in a condition where the capillary tube is pinched to a closed condition.

As is apparent from FIG. 4, each receptacle 46 and the capillary tube 44 communicating therewith may be made in one piece of a suitable plastic, for example, and each capillary tube 44 is flexible so that it can be pinched over as shown at the upper part of FIG. 4 with a suitable clip, string, or the like 48 placed around the pinched capillary tube for tightly closing the latter. In this condition it is possible to retain a fluid 50 such as blood or the like which has been collected in the receptacle 46 so that the device as shown in FIG. 4 may be transported, by mail, to a suitable laboratory. It will thus be seen that the embodiments of FIGS. 3 and 4 also provide for the receiving means formed by the several receptacles 46 passage means formed by the several tubes 44 which provide a predetermined degree of restriction to the flow of fluid for controlling the characteristics of the fluid collected by receptacles 46.

Prior to embedding of the receptacles 46 and the capillary tubes 44 in the tampon, 40, as illustrated in FIG. 3, or subsequent to such embedding, it is possible to introduce into the receptacles 46, through the tubes 44, for example, any of the additives referred to above in connection with FIG. 1, or any combination of these additives, as was the case with FIG. 1 as well as with FIG. 2, so that in this way the received fluid can have predetermined characteristics when collected in each receptacle 46.

Where any of the methods and devices of the invention are to be used with blood, a blood preservative such as citric acid may be incorporated in the devices.

What is claimed is:

1. In a method for collecting and analyzing body fluids, the steps of introducing into a body cavity where the body fluid is present a device having an interior for receiving and holding the body fluid and also having a passage means which restricts the flow of the fluid to said hollow interior by a predetermined extent so that the fluid received in said hollow interior will have characteristics determined by the extent of restriction of flow provided by said passage means, and after said device has remained in said cavity for a length of time sufficient for the body fluid to be received in said hollow interior removing the device from the body cavity and thereafter testing the body fluid received in said hollow interior, the device having a plurality of interior portions respectively communicating through passage means of different degrees of restriction with the fluid so that the different interior portions will have fluid of different characteristics, each passage means and interior portion communicating therewith being in the form of a separate tube having an inner collecting end forming the hollow interior, and pinching said tube after fluid has been collected in a hollow interior communicating therewith so that the pinched tube with the fluid in the hollow interior space communicating therewith can be delivered to a location where the fluid can be tested.

2. A device for collecting body fluids, when the device is situated in a body cavity, comprising receiving means having a plurality of interior portions for receiving a body fluid, and a plurality of passage means respectively communicating with said plurality of interior portions of said receiving means for directing the body fluid thereto, said plurality of passage means respectively having free cross-sectional areas providing flow paths for the body fluid, and said areas of said flow paths of said passage means respectively having different sizes for providing different predetermined degrees of restriction to fluid flow for controlling characteristics of the fluids received respectively in said plurality of interior portions of said receiving means.

3. The combination of claim 2 and wherein a container has an open end through which body fluid can enter the interior of said container, said container having inwardly of its open end one of said interior portions forming part of said receiving means, and a filter extending across and carried by said container outwardly of said interior thereof and having a predetermined degree of fineness so that said filter forms one of said passage means with the fineness of said filter restricting the flow to control the characteristics of the fluid received in said one interior portion of said container.

4. The combination of claim 3 and wherein at least a pair of filters respectively form a pair of said passage means and are spaced from each other and extend across the interior of said container so that said filters can form an outer filter and an inner filter, said outer filter being coarser than said inner filter so that fluid having different characteristics will be collected in said container in a pair of said interior portions respectively situated on opposite sides of said inner filter, and said container carrying at opposite sides of said inner filter a pair of plugs which can be removed for respectively discharging fluid collected respectively on opposite sides of said inner filter.

5. The combination of claim 2 and wherein a plurality of sponge bodies are arranged in engagement with each other with an innermost sponge body surrounded and engaged by the next outer sponge body, and the innermost sponge body having the smallest cells while the next outer sponge body has cells coarser than said smallest cells, and so on, so that in the several sponge bodies which have cells of gradually smaller size progressing from the outermost sponge body toward the innermost sponge body body fluids of different characteristics will be collected, each inner sponge body forming an interior portion of said receiving means for receiving and holding a body fluid while the next outer sponge body forms a passage means for restricting the flow of body fluid.

6. The combination of claim 8 and wherein an additive is located in at least one of said interior portions of said receiving means for controlling the nature of the fluid retained in said one interior portion.

7. A device for collecting body fluids, comprising receiving means having a plurality of interior portions for receiving a body fluid, and a plurality of passage means respectively communicating with said plurality of interior portions of said receiving means for directing the body fluid thereto, said plurality of passage means respectively having different predetermined degrees of restriction for controlling characteristics of the fluids received respectively in said plurality of interior portions of said receiving means, one interior portion of said receiving means being in the form of a hollow receptacle while one of said passage means is in the form of a capillary tube communicating with said hollow receptacle.

8. The combination of claim 8 and wherein said capillary tube is flexible so that it can be pinched to a closed position for retaining fluid collected in said receptacle.

9. A device for collecting body fluids, comprising receiving means having an interior portion for receiving a body fluid, and passage means communicating with said receiving means for directing the body fluid thereto, said passage means having a predetermined degree of restriction for controlling characteristics of the fluid received in said receiving means, said receiving means being in the form of a hollow receptacle while said passage means is in the form of a capillary tube communicating with said hollow receptacle, a tampon having said capillary tube and receptacle embedded therein with an end of said capillary tube distant from said receptacle remaining open at an outer surface of said tampon.

10. The combination of claim 9 and wherein a plurality of said receptacles and a plurality of capillary tubes communicating therewith are embedded in said tampon with all of said tubes having open ends situated at said surface of said tampon, and said tubes respectively having different interior diameters for providing different degrees of restriction to flow of fluid into said receptacles.

11. The combination of claim 10 and wherein said tubes are flexible so that they can be pinched to be temporarily closed for retaining fluid in said receptacles.

* * * * *

UNITED STATES PATENT AND TRADEMARK OFFICE
CERTIFICATE OF CORRECTION

PATENT NO. : 3,958,561
DATED : May 25, 1976
INVENTOR(S) : Louis Bucalo

It is certified that error appears in the above—identified patent and that said Letters Patent are hereby corrected as shown below:

Column 6, line 36, change "8" to --2--; line 54, change "8" (second occurrence) to --7--.

Signed and Sealed this

Twenty-ninth Day of March 1977

[SEAL]

Attest:

RUTH C. MASON
Attesting Officer

C. MARSHALL DANN
Commissioner of Patents and Trademarks